United States Patent
Brown

(10) Patent No.: US 10,213,260 B2
(45) Date of Patent: Feb. 26, 2019

(54) END FIRE FIBER ARRANGEMENTS WITH IMPROVED EROSION RESISTANCE

(71) Applicant: Joe Denton Brown, Panama City, FL (US)

(72) Inventor: Joe Denton Brown, Panama City, FL (US)

(*) Notice: Subject to any disclaimer, the term of this patent is extended or adjusted under 35 U.S.C. 154(b) by 1551 days.

(21) Appl. No.: 13/692,512

(22) Filed: Dec. 3, 2012

(65) Prior Publication Data

US 2013/0345686 A1    Dec. 26, 2013

Related U.S. Application Data

(60) Provisional application No. 61/565,672, filed on Dec. 1, 2011, provisional application No. 61/721,104, filed on Nov. 1, 2012.

(51) Int. Cl.
*A61B 18/20* (2006.01)
*A61B 18/22* (2006.01)

(52) U.S. Cl.
CPC ...... *A61B 18/22* (2013.01); *A61B 2018/2222* (2013.01); *A61B 2018/2238* (2013.01); *A61B 2018/2272* (2013.01)

(58) Field of Classification Search
CPC ............... A61B 18/22; A61B 2018/22; A61B 2018/2238; A61B 2018/2255; A61B 2018/2261; A61B 2018/2272; A61B 2018/2285; A61B 2018/2288
USPC ..... 606/3, 13–19; 607/88–92; 600/101, 104, 600/114, 135, 136, 139, 143
See application file for complete search history.

(56) References Cited

U.S. PATENT DOCUMENTS

| | | | | |
|---|---|---|---|---|
| 4,913,142 A | * | 4/1990 | Kittrell | A61B 1/00096 606/15 |
| 5,257,991 A | * | 11/1993 | Fletcher et al. | 606/17 |
| 5,363,458 A | * | 11/1994 | Pan | A61B 18/22 385/128 |
| 7,226,444 B1 | * | 6/2007 | Ellman | A61B 18/22 606/15 |
| 8,425,500 B2 | * | 4/2013 | Hanley | A61B 18/24 29/426.2 |
| 2002/0188285 A1 | * | 12/2002 | Brown | A61B 18/24 606/15 |
| 2002/0193781 A1 | * | 12/2002 | Loeb | A61B 18/1402 606/15 |
| 2005/0131399 A1 | * | 6/2005 | Loeb | A61B 18/24 606/15 |
| 2005/0131400 A1 | * | 6/2005 | Hennings | A61B 18/24 606/15 |

(Continued)

*Primary Examiner* — Ahmed Farah
(74) *Attorney, Agent, or Firm* — Bacon & Thomas, PLLC

(57) ABSTRACT

An end-firing optical fiber includes protective ferrule through which treatment radiation is fired in an axial direction, the protective ferrule having refractive properties that cause the radiation to disperse laterally and/or the fiber having sufficient flexibility to enable the fiber to be aimed at a tissue situated to the side of the axis along which the fiber was inserted. The fiber and protective ferrule may be mounted in a cannula, with the cannula being sufficiently flexible to enable the cannula to be withdrawn into a scope having a straight working channel, but has a pre-formed curvature that enables treatment of lateral tissues when the cannula is extended out of a scope.

8 Claims, 4 Drawing Sheets

(56) References Cited

U.S. PATENT DOCUMENTS

| | | | |
|---|---|---|---|
| 2005/0154379 A1* | 7/2005 | McGowan, Sr. | A61F 9/008 606/4 |
| 2007/0270788 A1* | 11/2007 | Nahen et al. | 606/15 |
| 2008/0195085 A1* | 8/2008 | Loeb | 606/3 |
| 2009/0221994 A1* | 9/2009 | Neuberger | A61B 18/24 606/7 |
| 2009/0240242 A1* | 9/2009 | Neuberger | A61B 18/24 606/7 |
| 2009/0287198 A1* | 11/2009 | Hanley | A61B 18/24 606/15 |

\* cited by examiner

US 10,213,260 B2

END FIRE FIBER ARRANGEMENTS WITH IMPROVED EROSION RESISTANCE

This application claims the benefit of provisional U.S. Patent Application Ser. Nos. 61/565,672, filed Dec. 1, 2011, and 61/721,104, filed Nov. 1, 2012, each of which is incorporated by reference herein.

BACKGROUND OF THE INVENTION

1. Field of the Invention

This invention relates to optical fibers used in laser treatment applications such as, by way of example and not limitation, benign prostate hypertrophy (BPH) treatments.

The invention replaces a side-firing optical fiber surrounded by a protective end cap with one of the following end-firing optical fiber arrangements:

(i) an end-firing optical fiber having a protective ferrule welded to the optical fiber, the index of refraction of the ferrule being matched to that of the fiber to cause dispersal of laser energy and increase the firing angle of the laser, or (ii) an end-firing optical fiber and protective ferrule mounted in a cannula, the cannula having a pre-formed curvature that enables treatment of lateral tissues when the cannula is extended out of a scope, but that is sufficiently flexible to enable the cannula to be withdrawn into a scope having a straight working channel.

By directing treatment radiation in an axial or "end-fire" rather than side-firing direction, the thickness or length of the material through which the treatment radiation is directed can be increased without limitation due to the size of the working channel through which the optical fiber and ferrule are inserted.

2. Description of Related Art

FIG. 1A shows a conventional side firing fiber arrangement for surgical applications. The conventional fiber arrangement typically uses a 600 micron fiber 1 having a beveled tip 52 at a distal or exit end of the fiber to reflect laser energy L laterally from the laser axis. The lateral reflection uses principles of total internal reflection. To maintain the total internal reflection in a fluid environment, such as a vein or within the urinary tract, a quartz cap 53 covers the beveled tip.

The quartz cap 53 of the conventional arrangement shown in FIG. 1 typically is limited to a maximum outer diameter OD of 1.8 mm and an internal diameter ID of about 1 mm. This limits the wall thickness of the cap 53 to about 400 microns. During lasing into soft tissue, the surface of the cap begins to erode due to free electron absorption when the temperature of the cap exceeds one thousand degrees in the area through which the laser is directed. This erosion on the surface of the cap scatters the energy, thereby lowering the power density and efficiency of vaporizing tissue.

Normally, the temperature of the end cap 53 will not exceed one thousand degrees during a BPH treatment. However, when contact is made with the tissue being treated, such as prostate tissue during a BPH treatment, the temperature of the cap can rise rapidly, and a hole can appear before the operator is aware of the problem. The fluid migrating through the hole will cause the angle tip to cease functioning and the treatment radiation to instead cause internal heating in the area of the fiber tip. This internal heating not only can damage the fiber tip, it may even cause the cap to explode.

FIGS. 1B and 1C illustrate the erosion process in more detail. In these figures, reference numeral 27 indicates a conventional side fire probe including a side fire fiber 36 having an angled tip 40 enclosed within a fused silica cap 15. Cap 15 extends from a ferrule 35 that is secured to the fiber 36. The angled tip causes treatment radiation to be directed through the cap in an area 16 positioned between the fiber 36 and the tissue to be treated. As with the arrangement illustrated in FIG. 1A, the cap 15 shown in FIGS. 2A and 2B may erode in the area 16 through which the treatment radiation is directed, allowing fluid migration into the cap. Reference numeral 28 indicates the side fire probe 27, after erosion has created a hole 19, permitting ingress of fluid and excessive heating in the vicinity 18 of the tip of fiber 36.

One possible solution to the problem of erosion would be to simply increase the wall thickness of the cap 15. However, such an increase in thickness is not possible for many applications because the overall diameter of the cap 15 is limited by the diameter of the working channel of the scope through which it is extended. As noted above, for example, the maximum diameter of a cap used in BPH treatment is about 1.8 millimeters because the cap is required to fit into the working channel of a cystoscope used in BPH treatment is about 1.8 millimeters.

SUMMARY OF THE INVENTION

It is accordingly an objective of the invention to provide an optical fiber for surgical applications, the optical fiber being surrounded by a protective cap designed to prevent contact between irrigation fluid and a tip of the fiber, in which the protective cap is not subject to erosion due to contact between the cap and a tissue being treated.

It is a further objective of the invention to provide an optical fiber for surgical applications, the optical fiber being surrounded by a protective cap designed to prevent contact between irrigation fluid and a tip of the fiber, in which the protective cap has improved resistance to erosion without increased wall thickness so as to enable the protective cap to fit within a standard-sized cannula for the particular surgical application in which the cannula is used.

These objectives are accomplished by replacing the side-firing optical fiber with an end-firing optical fiber, and by replacing the conventional end cap with a protective ferrule that extends beyond the end of the fiber and through which laser energy is directed in an axial direction relative to the axis of the optical fiber. By providing such an end-firing fiber arrangement, it becomes possible to treat laterally-situated tissues while increasing the thickness or length of the ferrule material through which the treatment radiation is directed without affecting the ability of the fiber and ferrule to fit within a standard scope, thereby reducing the possibility that erosion of the cap will allow fluid migration into the cap and cause overheating or an explosion.

In a first preferred embodiment of the invention, the end-firing optical fiber is provided with sufficient flexibility to enable the fiber to be easily bent in order to direct the laser energy at a desired surface, and the ferrule is a quartz ferrule welded to the distal end of the fiber, the quartz ferrule having an index of refraction matched to that of the fiber so that the laser energy delivered by the fiber disperses to increase the firing angle of the laser.

In a second preferred embodiment of the invention, the end-firing optical fiber and a surrounding ferrule are mounted in a flexible cannula having a pre-formed curvature that is assumed when the cannula is extended out of a scope to direct the treatment radiation in a lateral direction and enable the treatment radiation to be directed toward tissues at the side of the fiber. The cannula is made flexible to permit the fiber to be straightened when inserted or pulled into the rigid scope, the cannula assuming its pre-formed curved shape whenever it is no longer confined by the working channel of the scope. In this embodiment, the optical fiber may be fused to the ferrule, or extendable with respect to the ferrule to permit the fiber to be extended into the ferrule as it is eroded, extending the life of the fiber, or to be moved forwards or backwards to control a power density of radiation incident on a target tissue.

In each of the preferred embodiments of the invention, the tip of the ferrule may be recessed to reduce the risk of contact between the fiber tip and the tissue being treated, or may be left open to permit ingress of irrigation fluid.

DETAILED DESCRIPTION OF THE PREFERRED EMBODIMENTS

Figure 2A:
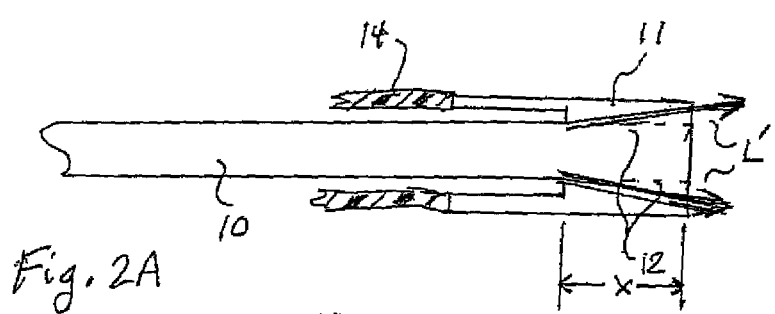
FIGS. 2A and 2B are side views of the first preferred embodiment of the invention.
Figure 2B:
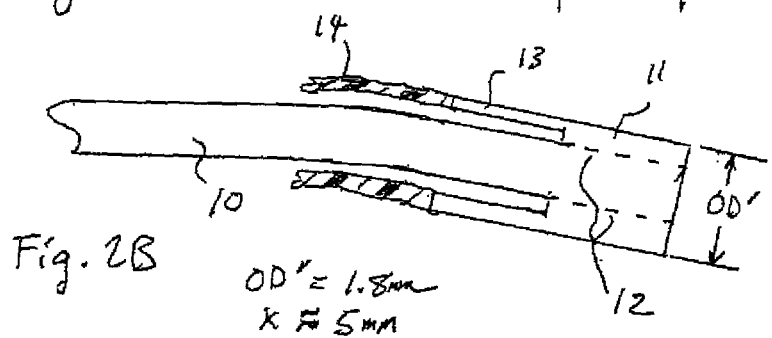

FIGS. 2A and 2B show an embodiment of the present invention that includes an end-firing optical fiber 10 and a quartz ferrule 11 welded to the distal end of the fiber 10.

In this embodiment, fiber 10 is preferably sufficiently flexible to enable the fiber to be bent in order to direct laser energy at a desired surface situated to the side of the optical fiber. The ferrule 11 is preferably a quartz ferrule 11 has an index of refraction matched to that of the fiber 10, laser energy L' disperses to increase the firing angle of the laser.

The length X of the welded area 12 between the fiber 10 and the ferrule 11 is typically 5 mm or greater. This extended weld gives the fiber 12.5 times greater erosion protection and ensures that the power density will remain high in comparison with a capped fiber arrangement as the power is contained inside the core of the fiber. Those skilled in the art will appreciate that, in this embodiment, the weld can be to the fiber's core or cladding, and that the cap may include an extension 13 for attachment to the fiber sheath 14. The distal tip can also be polished at various angle or shapes.

Figure 3:
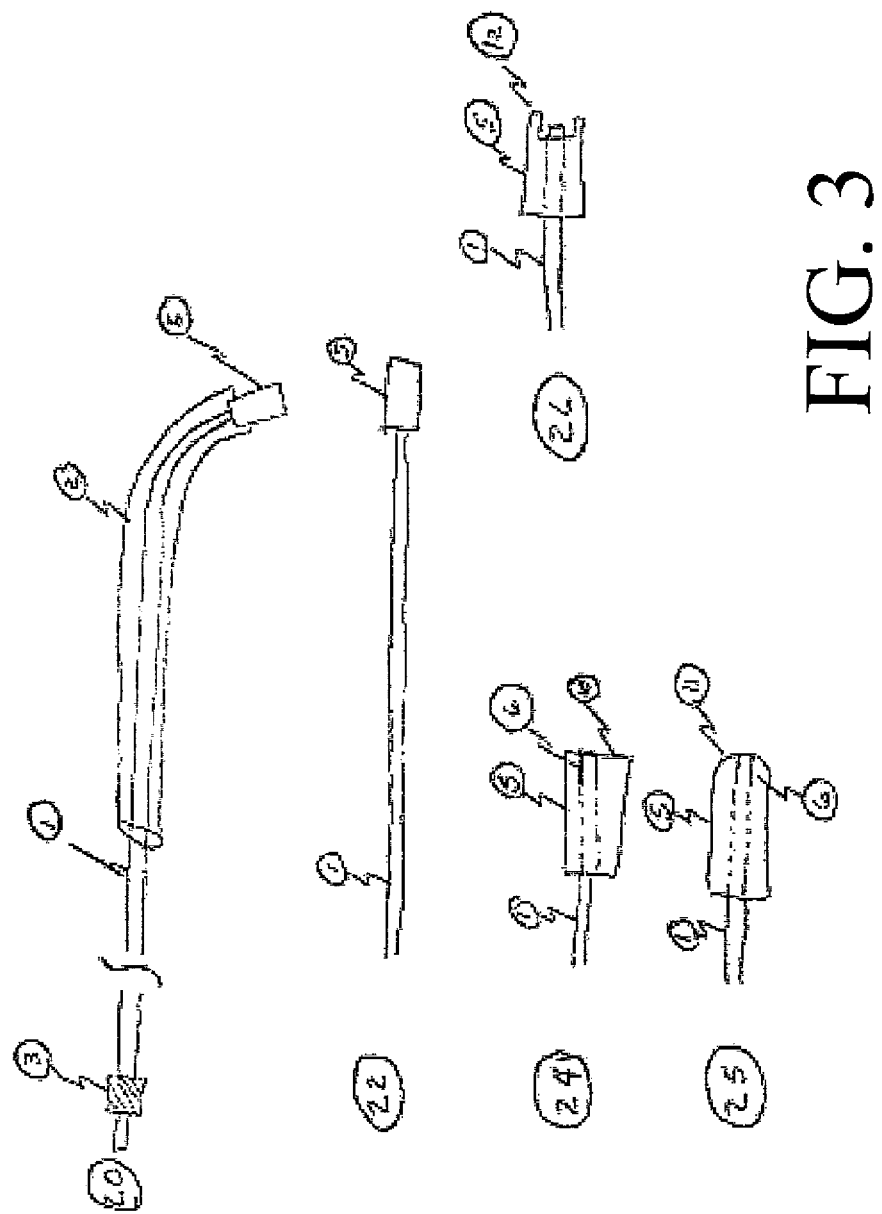
FIG. 3 includes side view of the second preferred embodiment of the invention.

FIG. 3 shows variations of an end-firing fiber arrangement in accordance with a second preferred embodiment of the invention. In the arrangement indicated by reference numeral 20 of FIG. 3, a small, flexible, end-firing optical fiber 1 without an angled tip is fused to a quartz ferrule 6, and the fiber 1 and ferrule 6 are mounted in a pre-formed flexible cannula 2 whose unstressed shape is a curvature that causes the fiber end to point laterally and enable treatment radiation to be directed to tissues situated at the side of the fiber insertion axis. The flexible cannula 2 is preferably made of a shape memory material with sufficient flexibility to cause the cannula to straighten, as indicated by reference numeral 22, upon withdrawal or insertion into the straight working channel of a cystoscope or other scope or introducer (not shown), but that returns to the curved shape when extended out of the scope.

As a result of this arrangement, the material of the ferrule situated between the end of the fiber and the tissue, at which treatment radiation is directed, can be made as thick as desired while still permitting the treatment radiation to be directed at lateral tissues, and without affecting the ability of the fiber and ferrule to fit within the working channel of a standard cystoscope or other scope having a limited working channel diameter.

Reference numeral 24 indicates a close-up of the ferrule 5 in the arrangement indicated by reference numerals 20 and 22. As illustrated, the fuse length 6 can be adjusted along the ferrule length 15 to 6 mm or more, giving at least three times more erosion before a hole is formed, as compared to the 1.8 mm thickness limitation to which the side firing fiber and cap of the prior art is subject, as discussed above. The tip 15 of this example is flat polished, although a rounded tip may also be provided, as indicated by reference numeral 25.

As an alternative to the fused ferrule 5 of the arrangements indicated by reference numerals 20, 22, 24, and 25, a non-fused fiber and ferrule arrangement may be provided, as indicated by reference numeral 26. In this arrangement, the tip 12 of the non-fused ferrule 5 may be recessed to keep the tip from being sunk into prostate or other tissue being treated. Since the fiber 1 is not fused to the ferrule 5 in this example, the fiber can be extended into the ferrule as it is eroded, in a manner analogous to extension of the lead in a mechanical pencil, giving more life to the fiber over a given procedure.

Figure 1A:
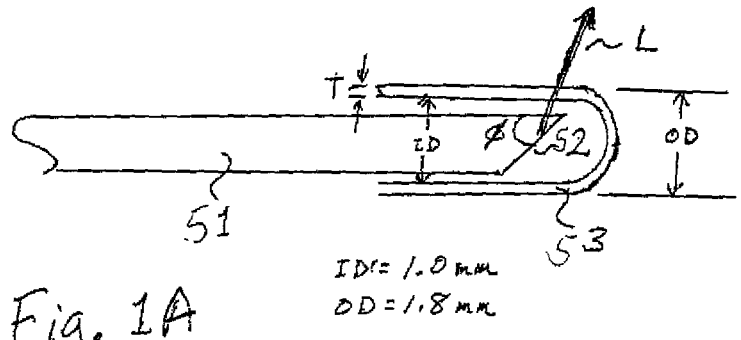
FIGS. 1A-1C are side views of conventional side fire arrangements.
Figures 1B, 1C:
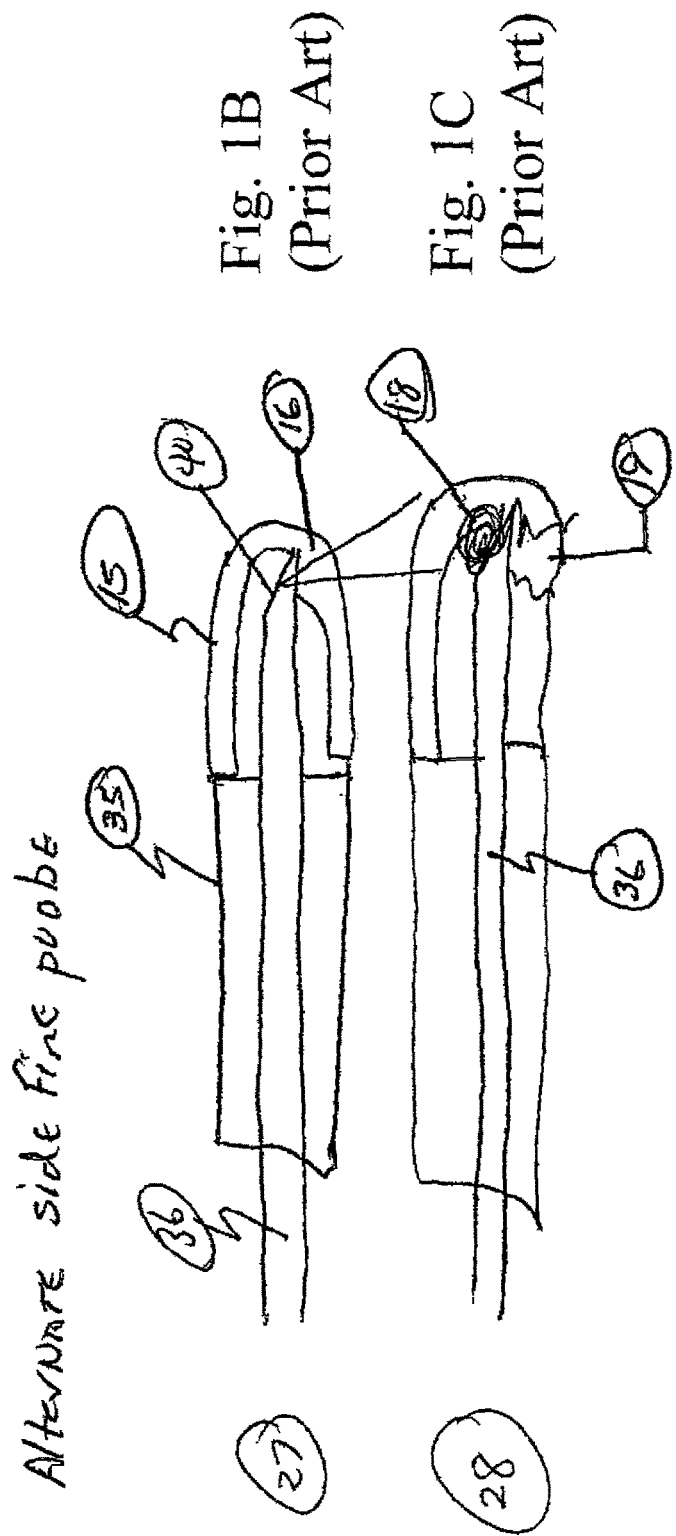
Figure 4:
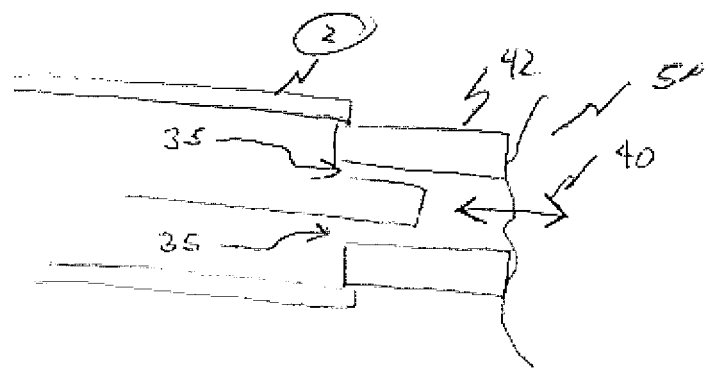
FIG. 4 is a side view of a movable-fiber arrangement according to a variation of the preferred embodiments illustrated in FIG. 3.

FIG. 4 shows a variation of the non-fused arrangement of FIG. 1, in which a quartz ferrule 42 corresponding to ferrule 5 of FIG. 1 is secured to the cannula 2 and the fiber is free to be positioned within the ferrule, as indicated by arrow 40. In this variation, irrigation fluid 35, such as water, saline, or air, is permitted to enter the ferrule 42, and the fiber is capable of being moved forward or backwards to increase or decrease a power density of radiation incident on a tissue 50 positioned directly in front of the ferrule 42.

Having thus described preferred embodiments of the invention in connection with the accompanying drawings, it will be appreciated that the invention is not to be limited to the specific embodiments or variations disclosed.

I claim:

1. An arrangement for delivering treatment radiation to tissues situated laterally of an optical fiber through which the treatment radiation is delivered, comprising:
   a protective ferrule surrounding and enclosing a treatment end of an optical fiber adjustably positioned within the protective ferrule; and
   a cannula in which the optical fiber and protective ferrule are mounted, wherein:
   treatment radiation is emitted axially from an end of the optical fiber through the protective ferrule,
   the cannula has a pre-formed curvature,
   the curvature of the cannula is assumed by the optical fiber mounted therein to cause treatment radiation emitted axially through an end of the fiber to be directed laterally at tissues situated to a side of the fiber, and
   the cannula has sufficient flexibility to enable the cannula and fiber to straighten when withdrawn into a straight working channel of a scope, the cannula and fiber returning to the pre-formed curvature when extended out of the working channel.

2. An arrangement as claimed in claim 1, wherein the ferrule is a quartz ferrule.

3. An arrangement as claimed in claim 1, wherein a tip of the ferrule is flat.

4. An arrangement as claimed in claim 1, wherein a tip of the ferrule is rounded.

5. An arrangement as claimed in claim 1, wherein a tip of the ferrule is recessed.

6. An arrangement as claimed in claim 1, for use in prostate tissue treatment applications.

7. An arrangement for delivering treatment radiation to tissues situated laterally of an optical fiber through which the treatment radiation is delivered, comprising:
   a protective ferrule surrounding a treatment end of an optical fiber; and
   a cannula to which the protective ferrule is mounted, wherein:
   treatment radiation is emitted axially from an end of the optical fiber through the protective ferrule,
   the cannula has a pre-formed curvature,
   the curvature of the cannula is assumed by the optical fiber mounted therein to cause treatment radiation emitted axially through an end of the fiber to be directed laterally at tissues situated to a side of the fiber,
   the cannula has sufficient flexibility to enable the cannula and fiber to straighten when withdrawn into a straight working channel of a scope, the cannula and fiber returning to the pre-formed curvature when extended out of the working channel, and
   the fiber is movable within the ferrule to control power density of treatment radiation incident on a tissue situated in front of the ferrule.

8. An arrangement for delivering treatment radiation to tissues situated laterally of an optical fiber through which the treatment radiation is delivered, comprising:
   a protective ferrule surrounding and enclosing a treatment end of an optical fiber; and a cannula in which the optical fiber and protective ferrule are mounted, wherein:
   treatment radiation is emitted axially from an end of the optical fiber through the protective ferrule,
   the cannula has a pre-formed curvature,
   the curvature of the cannula is assumed by the optical fiber mounted therein to cause treatment radiation emitted axially through an end of the fiber to be directed laterally at tissues situated to a side of the fiber, and
   the cannula has sufficient flexibility to enable the cannula and fiber to straighten when withdrawn into a straight working channel of a scope, the cannula and fiber returning to the pre-formed curvature when extended out of the working channel,
   wherein a tip of the ferrule is recessed, and
   wherein an end of the ferrule is open to permit ingress of irrigation fluid.

* * * * *